(12) United States Patent
Belliotti et al.

(10) Patent No.: US 6,627,771 B1
(45) Date of Patent: Sep. 30, 2003

(54) GAMMA AMINO BUTYRIC AND ACID ANALOGS

(75) Inventors: Thomas Richard Belliotti, Saline, MI (US); David Juergen Wustrow, Ann Arbor, MI (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 09/807,480

(22) PCT Filed: Nov. 2, 1999

(86) PCT No.: PCT/US99/25569
§ 371 (c)(1),
(2), (4) Date: Apr. 13, 2001

(87) PCT Pub. No.: WO00/31020
PCT Pub. Date: Jun. 2, 2000

Related U.S. Application Data

(60) Provisional application No. 60/109,830, filed on Nov. 25, 1998.

(51) Int. Cl.[7] .................. C07C 205/00; C07C 229/00
(52) U.S. Cl. ................. 562/553; 562/443; 562/553; 562/567; 562/571; 562/568; 514/385; 514/585; 514/561
(58) Field of Search ................. 562/553, 443, 562/561, 567, 568, 571; 514/385, 585, 561

(56) References Cited

U.S. PATENT DOCUMENTS

| 4,087,544 A | | 5/1978 | Satzinger et al. ......... 424/305 |
| 5,563,175 A | * | 10/1996 | Silverman et al. |
| 5,599,973 A | * | 2/1997 | Silverman et al. |
| 5,608,090 A | * | 3/1997 | Silverman et al. |
| 5,684,189 A | * | 11/1997 | Silverman et al. |
| 5,710,304 A | * | 1/1998 | Silverman et al. |

FOREIGN PATENT DOCUMENTS

| EP | 0023192 | | 3/1984 |
| JP | 01272522 A | | 10/1989 |
| WO | 9209560 | | 6/1992 |
| WO | WO 92/09560 | * | 6/1992 |
| WO | 9323383 | | 11/1993 |
| WO | WO 93/233383 | * | 11/1993 |
| WO | 9817627 | | 4/1998 |

OTHER PUBLICATIONS

Petter et al, J. Organic Chemistry, 1990, 55, pp. 3088–3097.*
Suman–Chauhan et al, European J. of Pharm. MolecularBiology Section, 1993, 244, pp. 293–301.*
Sivelverman et al, J. Medicinal Chemistry, 1991, 34, pp. 2295–2298.*
Suman–Chauhan et al, European Journal of Pharmacology, Molecular Biology Section, 1993, 224, pp. 293–301.*
Silverman et al, Journal of Medicinal Chemistry, 1991, vol. 34, pp. 2295–2298.*
PCT International Search Report, PCT/US99/25569.
Silverman et al., "3–Alkyl–4–aminobutyric Acids: The First Class of Anticonvulsant Agents That Activates L–Glutamic Decarboxylase", *J. Med. Chem.*, vol. 34, No. 7, 1991, pp. 2295–2298.
Petter et al., "Inhibition of γButyrbetaine Hydroxylase by Cyclopropyl–Substituted γButyrobetaines", *J. Org. Chem.*, vol. 55, No. 10, 1990, pp. 3088–3097.
Suman–Chauhan et al., "Characterization of [3H]gabapentin binding to a novel site in rat brain: Homogenate binding studies", *Eur. J. Pharmacol.*, Mol. Pharmacol. Sect. (1991), 244(3), 293–301 (CAPLUS 118:182788, abstract only).
Kovalev et al., "Synthesis of some .gamma.–aminobutyric acid derivatives and a study of their effect on the accumulation of labeled [3H].gamma.–aminobutyric acid by brain synaptosomes", *Khim.–Farm. Zh.*, (1979), 13(10), 18–23 (CSPLUS 92:94193, abstract only).

* cited by examiner

Primary Examiner—Alan L. Rotman
Assistant Examiner—Hector M Reyes
(74) Attorney, Agent, or Firm—Peter C. Richardson; Lorraine B. Ling

(57) ABSTRACT

The instant invention is improved gamma amino butyric acid analogs, processes for their preparation, and methods of using them as agents for treating epilepsy and other neurodegenerative disorders, depression, anxiety, panic, pain, neuropathological disorders, gastrointestinal damage, and inflammation.

12 Claims, No Drawings

GAMMA AMINO BUTYRIC AND ACID ANALOGS

This application is a 371 of PCT/US99/25569 Nov. 2, 1999 which claims benefit of No. 60/109,830 Nov. 25, 1998.

BACKGROUND

Compounds of formula

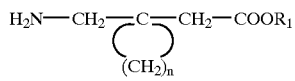

wherein $R_1$ is hydrogen or a lower alkyl radical and n is 4, 5, or 6 are known in U.S. Pat. No. 4,024,175 and its divisional U.S. Pat. No. 4,087,544. The uses disclosed are: protective effect against cramp induced by thiosemicarbazide; protective action against cardiazole cramp; the cerebral diseases, epilepsy, faintness attacks, hypokinesia, and cranial traumas; and improvement in cerebral functions. The compounds are useful in geriatric patients. The patents are hereby incorporated by reference.

Compounds of formula

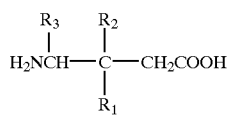

wherein $R_1$ is a straight or branched alkyl group having from 1 to 6 carbon atoms, phenyl, or cycloalkyl having from 3 to 6 carbon atoms; $R_2$ is hydrogen or methyl; and $R_3$ is hydrogen, methyl, or carboxyl are known in U.S. Pat. No. 5,563,175 and various divisionals. These patents are hereby incorporated by reference.

Compounds of formula

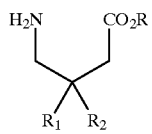

wherein R and $R_1$ are hydrogen or lower alkyl, and $R_2$ is

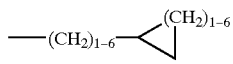

are known in U.S. Pat. Application No. 60/059900 filed Sep. 24, 1997, now abandoned and PCT/US97/17997 filed Oct. 7, 1997. This is also incorporated by reference.

SUMMARY OF THE INVENTION

The instant invention is compounds of Formula 1 below.

Preferred are compounds of Formula 1 wherein n is zero and R is hydrogen or methyl.

Especially preferred are 4-amino-3-cyclopentyl-butyric acid, (R)-4-amino-3-cyclopentyl-butyric acid, and (S)-4-amino-3-cyclopentyl-butyric acid.

Pharmaceutical composition containing one or more compounds of Formula 1 are part of the inventions.

The compounds are useful in the treatment of epilepsy, faintness attacks, hypokinesia, cranial disorders, neurodegeneration disorders, depression, anxiety, panic, pain, neuropathological disorders, treating gastrointestinal damage and inflammation.

DETAILED DESCRIPTION OF THE INVENTION

The instant invention is for certain compounds which exhibit improved activity in models of pain and epilepsy over those in U.S. Ser. No. 06/059900 now abandoned.

The compounds of the invention are those of Formula I

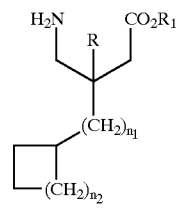

or a pharmaceutically acceptable salt thereof wherein:
$R_1$ is hydrogen or lower alkyl;
R is hydrogen or methyl;
$n_1$ is an integer of from 0 to 1; and
$n_2$ is an integer of from 0 to 3.

Since amino acids are amphoteric, pharmacologically compatible salts can be salts of appropriate inorganic or organic acids, for example, hydrochloric, sulphuric, phosphoric, acetic, oxalic, lactic, citric, malic, salicylic, malonic, maleic, succinic, methanesulfonic acid, and ascorbic. Starting from corresponding hydroxides or carbonates, salts with alkali metals or alkaline earth metals, for example, sodium, potassium, magnesium, or calcium are formed. Salts with quaternary ammonium ions can also be prepared with, for example, the tetramethyl-ammonium ion. The carboxyl group of the amino acids can be esterified by known means.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The terms used to define the invention are as described below.

The term "alkyl" is a straight or branched group of from 1 to 4 carbon atoms including but not limited to methyl, ethyl, propyl, n-propyl, isopropyl, butyl, 2-butyl, and tert-butyl.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

The radioligand binding assay using [$^3$H]gabapentin and the $\alpha_2\delta$ subunit derived from porcine brain tissue was used ("The Novel Anti-convulsant Drug, Gabapentin, Binds to the $\alpha_2\delta$ Subunit of a Calcium Channel", Gee N. S., et al., *J. Biol. Chem.*, 1996;271(10):5768–5776).

The compounds of the invention show good binding affinity to the $\alpha_2\delta$ subunit. Gabapentin (Neurontin®) is about 0.10 to 0.12 µM in this assay. Since the compounds of the instant invention also bind to the subunit, they are expected to exhibit pharmacologic properties comparable to gabapentin. For example, as agents for convulsions, anxiety, and pain.

TABLE 1

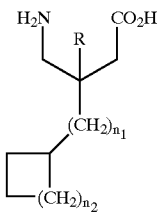

| Example | 3 Subst. R | Spacer $n_1$ | Ring size $n_2$ | System L Binding IC$_{50}$ (mM) | $\alpha_2\delta$ Assay IC$_{50}$ (µM) | Pain Model % MPE 1 Hour | Pain Model % MPE 2 Hour | DBA2 Mouse Model % Protected | Vogel Conflict % of CI-1008 |
|---|---|---|---|---|---|---|---|---|---|
| 1 | H | 0 | 0 | | 0.733 | | | 0 1, 2 hr | |
| 2 | H | 0 | 1 | 1.5 | 0.645 | −1.7 | −12.1 | 0 1 Hr @ 30 m/k<br>40 2 Hr @ 30 m/k | 2.48 |
| 3 | H | 0 | 2 | 0.464 | 0.133 | 73.8 | 27.7 | 40 1 Hr<br>40 2 Hr | 35.4 |
| 4R+ | H | 0 | 2 | 0.198 | 0.108 | 36 | 13.7 | 60 1 Hr<br>40 2 Hr | 52 |
| 5S− | H | 0 | 2 | 0.476 | 0.145 | 35 | 24 | 0 1 Hr<br>0 2 Hr | 0 |
| 6 | H | 1 | 0 | 1.87 | 0.626 | 2.3 | −3.4 | 20 2 Hr | 5.11 |
| 7 | H | 1 | 1 | 2.6 | 0.317 | 1.5 | −3.4 | 20 2 Hr | 2.96 |
| 8 | H | 1 | 2 | 4.64 | 3.18 | | | 0 1 Hr<br>0 2 Hr | −8.3 |
| 9 | H | 1 | 3 | 5.5 | 4.87 | | | | |
| 10 | Me | 0 | 0 | 0.599 | ca 10 | −4.3 | −9.1 | 0 1, 2 Hr | −8.13 |
| 11 | Me | 0 | 1 | 0.074 | >10 | 4.2 | 3.1 | 0 1, 2 Hr | 7.05 |
| 12 | Me | 1 | 1 | 0.105 | 0.8 | −4.2 | −5.2 | 0 1, 2 Hr | 0.3 |
| 13 | Me | 1 | 2 | 1.04 | >10 | | | | |

As can be seen in the above table, the R isomer of Example 4 is especially active in preventing convulsions, as an antihyperalgesic and as an antianxiety agent.

The compounds of the invention are related to Neurontin®, a marketed drug effective in the treatment of epilepsy. Neurontin® is 1-(aminomethyl)-cyclohexaneacetic acid of structural formula

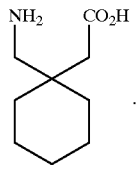

The compounds of the invention are also expected to be useful in the treatment of epilepsy.

The present invention also relates to therapeutic use of the compounds of the mimetic as agents for neurodegenerative disorders.

Such neurodegenerative disorders are, for example, Alzheimer's disease, Huntington's disease, Parkinson's disease, Amyotrophic Lateral Sclerosis, and epilepsy.

The present invention also covers treating neurodegenerative disorders termed acute brain injury. These include but are not limited to: stroke, head trauma, and asphyxia.

Stroke refers to a cerebral vascular disease and may also be referred to as a cerebral vascular incident (CVA) and includes acute thromboembolic stroke. Stroke includes both focal and global ischemia. Also, included are transient cerebral ischemic attacks and other cerebral vascular problems accompanied by cerebral ischemia such as in a patient undergoing carotid endarterectomy specifically or other cerebrovascular or vascular surgical procedures in general, or diagnostic vascular procedures including cerebral angiography and the like.

Pain refers to acute as well as chronic pain.

Acute pain is usually short-lived and is associated with hyperactivity of the sympathetic nervous system. Examples are postoperative pain and allodynia.

Chronic pain is usually defined as pain persisting from 3 to 6 months and includes somatogenic pains and psychogenic pains. Other pain is nociceptive.

Still other pain is caused by injury or infection of peripheral sensory nerves. It includes, but is not limited to pain from peripheral nerve trauma, herpes virus infection, diabetes mellitus, causalgia, plexus avulsion, neuroma, limb amputation, and vasculitis. Neuropathic pain is also caused by nerve damage from chronic alcoholism, human immunodeficiency virus infection, hypothyroidism, uremia, or vitamin deficiencies. Neuropathic pain includes, but is not limited to pain caused by nerve injury such as, for example, the pain diabetics suffer from.

Psychogenic pain is that which occurs without an organic origin such as low back pain, atypical facial pain, and chronic headache.

Other types of pain are: inflammatory pain, osteoarthritic pain, trigeminal neuralgia, cancer pain, diabetic neuropathy, restless leg syndrome, acute herpetic and postherpetic neuralgia, causalgia, brachial plexus avulsion, occipital neuralgia, gout, phantom limb, burn, and other forms of neuralgia, neuropathic and idiopathic pain syndrome.

Other incidents are head trauma, spinal cord trauma, or injury from general anoxia, hypoxia, hypoglycemia, and hypotension as well as similar injuries seen during procedures from embole, hyperfusion, and hypoxia.

The instant invention would be useful in a range of incidents, for example, during cardiac bypass surgery, in incidents of intracranial hemorrhage, in perinatal asphyxia, in cardiac arrest, and status epilepticus.

A skilled physician will be able to determine the appropriate situation in which subjects are susceptible to or at risk of, for example, stroke as well as suffering from stroke for administration by methods of the present invention.

The compounds of the invention are also expected to be useful in the treatment of depression. Depression can be the result of organic disease, secondary to stress associated with personal loss, or idiopathic in origin. There is a strong tendency for familial occurrence of some forms of depression suggesting a mechanistic cause for at least some forms of depression. The diagnosis of depression is made primarily by quantification of alterations in patients' mood. These evaluations of mood are generally performed by a physician or quantified by a neuropsychologist using validated rating scales, such as the Hamilton Depression Rating Scale or the Brief Psychiatric Rating Scale. Numerous other scales have been developed to quantify and measure the degree of mood alterations in patients with depression, such as insomnia, difficulty with concentration, lack of energy, feelings of worthlessness, and guilt. The standards for diagnosis of depression as well as all psychiatric diagnoses are collected in the Diagnostic and Statistical Manual of Mental Disorders (Fourth Edition) referred to as the DSM-IV-R manual published by the American Psychiatric Association, 1994.

GABA is an inhibitory neurotransmitter with the central nervous system. Within the general context of inhibition, it seems likely that GABA-mimetics might decrease or inhibit cerebral function and might therefore slow function and decrease mood leading to depression.

The compounds of the instant invention may produce an anticonvulsant effect through the increase of newly created GABA at the synaptic junction. If gabapentin does indeed increase GABA levels or the effectiveness of GABA at the synaptic junction, then it could be classified as a GABA-mimetic and might decrease or inhibit cerebral function and might, therefore, slow function and decrease mood leading to depression.

The fact that a GABA agonist or GABA-mimetic might work just the opposite way by increasing mood and thus, be an antidepressant, is a new concept, different from the prevailing opinion of GABA activity heretofore.

The compounds of the instant invention are also expected to be useful in the treatment of anxiety and of panic as demonstrated by means of standard pharmacological procedures.

MATERIAL AND METHODS

Carrageenin-Induced Hyperalgesia

Nociceptive pressure thresholds were measured in the rat paw pressure test using an analgesymeter (Randall-Sellitto Method: Randall L. O., Sellitto J. J., A method for measurement of analgesic activity on inflamed tissue. Arch. Int. Pharmacodyn., 4:409–419 (1957)). Male Sprague-Dawley rats (70–90 g) were trained on this apparatus before the test day. Pressure was gradually applied to the hind paw of each rat and nociceptive thresholds were determined as the pressure (g) required to elicit paw withdrawal. A cutoff point of 250 g was used to prevent any tissue damage to the paw. On the test day, two to three baseline measurements were taken before animals were administered 100 µL of 2% carrageenin by intraplantar injection into the right hind paw. Nociceptive thresholds were taken again 3 hours after carrageenin to establish that animals were exhibiting hyperalgesia. Animals were dosed with either gabapentin (3–300 mg/kg, s.c.), morphine (3 mg/kg, s.c.), or saline at 3.5 hours after carrageenin and nociceptive thresholds were examined at 4, 4.5, and 5 hours post carrageenin.

The compounds of the instant invention are also expected to be useful in the treatment of pain and phobic disorders (Am. J. Pain Manag., 5:7–9 (1995)).

Vogel Conflict

Vogel J. R., Beer B. and Cloody D. E., 1971, reported the procedure used. Basically, in each experiment, 100 naive adult male Wistar rats between 170–220 gm were randomly divided into 10 groups and deprived of water for 48 hours prior to testing. Food was available on Day 1 and removed 24 hours prior to test Day 2.

On Day 1, experimental subjects were placed into the test chambers and allowed to drink 5 mL of water unpunished from a drinking tube on a water bottle mounted on the outside of the chamber. Immediately following the unpunished drinking session, each rat was dosed (PO) with vehicle (1 mL/kg) and returned to their home cage. On test Day 2, rats are dosed with the appropriate treatment and placed in test cages, following a 2-hour absorption period each rat is placed into a test chamber and allowed to drink for 10 minutes. Adjacent to the drink-tube is an optical lickmeter with a photo beam detector that counts the number of licks during active drinking. Every 10 licks, the rats received 1-second shock (1 mA) through the drink tube. Thus, a conflict or anxiety-producing situation exists; rats are motivated to drink, however, they are inhibited by the shock. Anxiety is reflected by the low amounts of drinking. Standard anxiolytic drugs produce effects that allow rats to overcome this behavioral inhibition and drink despite the shock. Compounds that significantly increase the number of shock episodes over concurrently run controls, are presumed to possess anxiolytic properties.

DBA2 Mouse Model of Anticonvulsant Efficacy

All procedures were carried out in compliance with the NIH Guide for the Care and Use of Laboratory Animals under a protocol approved by the Parke-Davis Animal Use Committee. Male DBA/2 mice, 3 to 4 weeks old were obtained from Jackson Laboratories Bar Harbour, Maine. Immediately before anticonvulsant testing, mice were placed upon a wire mesh, 4 inches square, suspended from a steel rod. The square was slowly inverted through 180° and mice observed for 30 seconds. Any mouse falling from the wire mesh was scored as ataxic (Coughenour L. L., McLean J. R., Parker R. B., "A new device for the rapid measurement of impaired motor finction in mice," Pharm. Biochem. Behav., 1977;6(3):351–3). Mice were placed into an enclosed acrylic plastic chamber (21 cm height, approximately 30 cm diameter) with a high-frequency speaker (4 cm diameter) in the center of the top lid. An audio signal generator (Protek model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for one minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds. The incidence of all the seizure phases in the drug-treated and vehicle-treated mice was recorded, and the occurrence of tonic seizures were used for calculating anticonvulsant $ED_{50}$ values by probit analysis (Litchfield J. T., Wilcoxon F. "A simplified method for evaluating dose-effect experiments," *J. Pharmacol.*, 1949;96:99–113). Mice were used only once for testing at each dose point. Groups of DBA/2 mice (n=5–10 per dose) were tested for sound-induced seizure responses 2 hours (previously determined time of peak effect) after given drug orally. All drugs in the present study were dissolved in distilled water and given by oral gavage in a volume of 10 mL/kg of body weight. Compounds that are insoluble will be suspended in 1% carboxymethocellulose. Doses are expressed as weight of the active drug moiety.

The compounds of the instant invention are also expected to be useful in treating the symptoms of manic, acute or chronic, single upside, or recurring depression. They are also expected to be useful in treating and/or preventing bipolar disorder (U.S. Pat. No. 5,510,381).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula 1 or a corresponding pharmaceutically acceptable salt of a;compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 1 g according to the particular application and the potency of the active component. In medical use the drug may be administered three times daily as, for example, capsules of 100 or 300 mg. The composition can, if desired, also contain other compatible therapeutic agents.

In therapeutic use, the compounds utilized in the pharmaceutical method of this invention are administered at the initial dosage of about 0.01 mg to about 100 mg/kg daily. A daily dose range of about 0.01 mg to about 100 mg/kg is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day, if desired.

Scheme 1

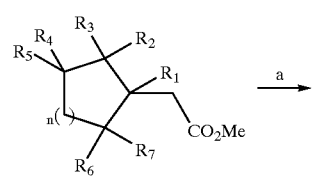

-continued

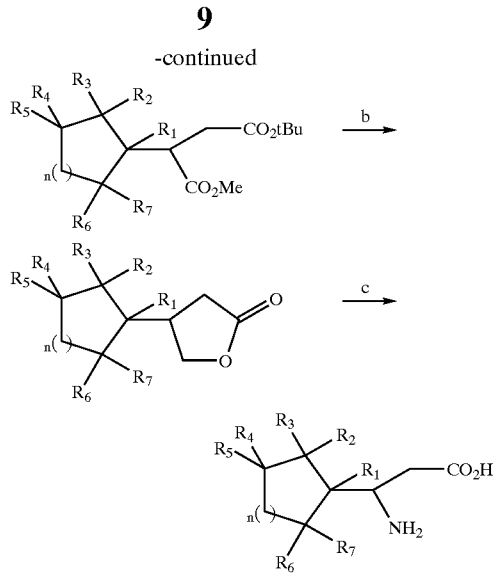

Reagents:

(a) LDA—78° BrCH$_2$CO$_2$tBu;

(b) 1) NaOH; 2) BH$_3$DMS; 3) PTSA;

(c) 1) HBr EtOH; 2) NaN$_3$; 3) H$_2$ Pd/C; 4) HCl.

Scheme 2

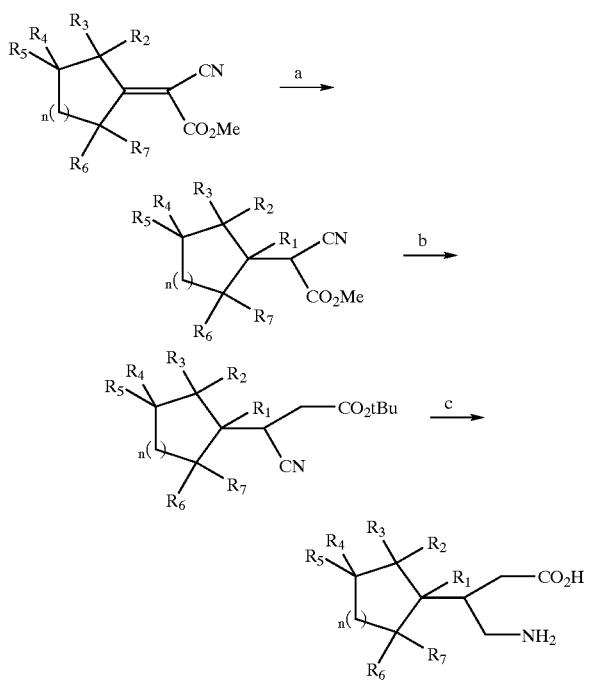

Reagents:

(a) R$_1$MgBr, CuI;

(b) 1) NaH, BrCH$_2$CO$_2$tBu; 2) NaOH;

(c) 1) H$_2$Pd/C; 2) HCl.

EXAMPLE 1
(4-Amino-3-cyclobutyl-butyric Acid)

This is prepared by tie method of Example 2 below.

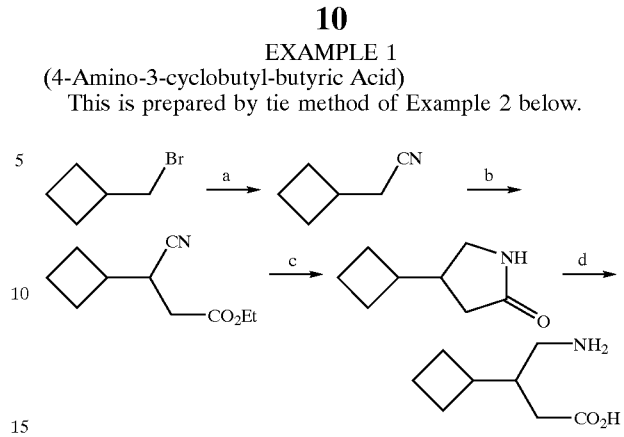

4-Amino-3-cyclobutyl-butyric Acid

Step A

Preparation of Cyclobutylacetonitrile—A solution of bromomethylcyclobutane (5.0 g, 33.5 mmol) and KCN (2.4 g, 36.9 mmol) in 50 mL of 15% H$_2$O/EtOH is warmed to reflux for 18 hours. The reaction mixture is diluted with 100 mL of brine and extracted with hexanes (3×100 mL). The combined extracts are dried over Na$_2$SO$_4$, and the solvent is removed by distillation through a vigreux column. The product remains in the pot. Residual hexane is removed by repeated (3×) addition and evaporation of Et$_2$O. Yield=6.0 g (71%) of cyclobutylacetonitrile. NMR ($^1$H, 400 MHz, CDCl$_3$) δ1.8 (4H, m); 2.2 (2H, m); 2.4 (2H, d); 2.7 (1H, m).

Step B

Preparation of 3-Cyclobutyl-3-cyano-propionic acid ethyl ester—Cyclobutylacetonitrile (3.0 g, 3.5 mmol) is added to a solution of freshly prepared LDA (31.5 mmol) in 50 mL of THF at −78° C. After being stirred at −78° C. for 5 minutes, the anion solution is added over 10 minutes by cannula to a solution of ethylbromoacetate in 100 mL of THF at −78° C. The solution is stirred for 2 hours, then quenched with 20 mL of 1.0N HCl and warmed to room temperature. The THF is evaporated. The organics are extracted into CH$_2$CL$_2$ (3×50 mL), and the extracts are dried over Na$_2$SO$_4$. The solvent is evaporated, and the remaining oil is chromatographed by MPLC in 10% EtOAc/Hexanes to give 0.5 g (9% yield) of 3-cyclobutyl-3-cyano-propionic acid ethyl ester as an oil. NMR ($^1$H, 400 MHz, CDCl$_3$)δ1.3 (3H, t); 1.8–2.2 (6H, m); 2.5 (2H, dd); 2.5 (1H, m); 3.0 (1H, m); 4.2(2H, q).

Step C

Preparation of 4-Cyclobutyl-pyrrolidin-2-one—A solution of 3-cyclobutyl-3-cyano-propionic acid ethyl ester (1.0 g, 5.5 mmol) in 50 mL of THF is treated with Raney Nickel under an H$_2$ atmosphere at room temperature for 5 hours. The solvent is evaporated, and the remaining oil is chromatographed (MPLC) in EtOAc. Yield=0.43 g (56%) of 4-cyclobutyl-pyrrolidin-2-one as an oil. NMR ($^1$H, 400 MHz, CDCl$_3$) δ1.7 (2H, m); 1.7–2.1 (6H, m); 2.3–2.4 (3H, m); 3.0 (1H, dd); 3.4 (1H, dd). Analysis for C$_8$H$_{13}$NO: Calculated: C, 69.03; H, 9.41; N, 10.06. Found: C, 68.84; H, 9.35, N, 9.97.

Step D

Preparation of 4-Amino-3-cyclobutyl-butyric acid—A solution of 4-cyclobutyl-pyrrolidin-2-one (0.43 g, 3.0 mmol) in 150 mL of 6.0N HCl is warmed to reflux for 12 hours. The solvent is evaporated, and the remaining solid is triturated with hot EtOAc. The isolated solid is dissolved in 15 mL of MeOH, and 20 mL of hot EtOAc is added. After 4 hours, a white precipitate forms which is collected and dried under vacuum with P$_2$O$_5$. Yield=0.31 g of 4-Amino-3-cyclobutyl-butyric acid as the HCl salt; mp=115–117° C. NMR ($^1$H, 400

MHz, DMSO)δ1.6 (4H, m); 1.9 (3H, m); 2.2 (2H, dd); 2.1 (1H, m); 2.6 (2H, m). Analysis for $C_8H_{15}NO_2$·HCl: Calculated: C, 49.61; H, 8.33; N, 7.23; Cl, 18.31. Found: C, 49.33; H, 8.27; N, 7.17; Cl,17.93.

EXAMPLE 3
4-Amino-3-cyclopentyl-butyric Acid

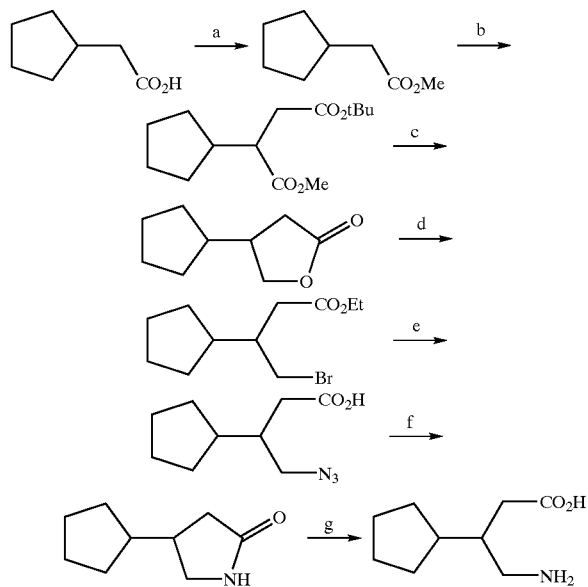

Step A preparation of cyclopentylacetic acid methyl ester—Cyclopentyl acetic acid (9.5 g, 74.1 mmol) is warmed to reflux in 300 mL of MeOH containing 10 mL of $H_2SO_4$ for 12 hours. The mixture is cooled to room temperature and diluted with 500 mL of $H_2O$. The solution is extracted with hexanes (3.200 mL). The combined extracts are washed with $H_2O$ (2.100 mL) and dried over $MgSO_4$. The solvent is removed by distillation through a vigreux column and the product remains in the pot. Residual hexane is removed by repeated (3×) addition and evaporation of $Et_2O$. Yield=9.4 g (89%) of cyclopentylacetic acid methyl ester as an oil. NMR ($^1$H, 400 MHz, CDCl$_3$) δ1.1 (2H, m); 1.6 (4H, m); 1.8 (2H, m); 2.2 ($^1$H, m); 2.3 (2H, d); 3.6 (3H, s).

Step B

Preparation of 2-Cyclopentyl-succinic acid 4-tert-butyl ester 1 -methyl ester—Cyclopentylacetic acid methyl ester (9.4 g, 66.1 mmol) is added to a solution of freshly prepared LDA (66.1 mmol) in 150 mL of THF at −78° C. under $N_2$ over 10 minutes. The solution is stirred at −78° C. for 10 minutes and then added by cannula to a solution of t-butylbromoacetate (19.3 g, 99.1 mmol) at −70° C. to −65° C. over 20 minutes. One hour after addition is complete, the reaction is allowed to warm to room temperature for 12 hours. It is quenched with 100 mL of saturated $KH_2PO_4$, and the THF is evaporated. The organics are extracted into $Et_2O$ (3×150 mL), and the combined extracts are dried over $MgSO_4$. The $Et_2O$ is evaporated, and the remaining oil is distilled under vacuum (0.1 mm Hg). B.P.=100–106° C. Yield of 2-cyclopentyl-succinic acid 4-tert-butyl ester 1-methyl ester=13.4 g (79%). NMR (1H, 400 MHz, CDCl$_3$) δ1.1 (1H, m); 1.3 (1H, m); 1.4 (9H, s); 1.3–1.4 (6H, m); 1.7 (1H, m); 1.9 (1H, m); 2.4 1H, d); 2.6 (2H, m); 3.6 (3H,s).

Step C

Preparation of 4-Cyclopentyl-dihydro-furan-2-one 2-Cyclopentyl-succinic acid 4-tert-butyl ester 1-methyl ester (13.4 g, 52.3 mmol) and LiOH·H$_2$O (2.8 g, 66.7 mmol) are stirred in 200 mL of 3:1 isopropanol/H$_2$O at room temperature overnight. The isopropanol is evaporated, and the aqueous solution is extracted with $Et_2O$ (3×100 mL). The aqueous phase is acidified to pH=4 with saturated $KH_2PO_4$ and extracted with $Et_2O$ (3×100 mL). The $Et_2O$ is dried over $MgSO_4$ and evaporated to give 8.6 g (68% yield) of 2-cyclopentyl-succinic acid 4-tert-butyl ester. NMR ($^1$H, 400 MHz, CDCl$_3$) δ1.1–1.3 (2H, m); 1.4 (9H, s); 1.5 (4H, m); 1.7 (2H, m); 1.9 (1H, m); 2.4 (1H, dt); 2.6 (2H, m). The product is carried on.

Borane dimethyl sulfide complex (3.5 mL, 10.0 M in THF) is added to a solution of 2-cyclopentyl-succinic acid 4-tert-butyl ester 1-methyl ester (8.6 g, 35.5 mmol) in 100 mL of THF at 0° C. The mixture is warmed to room temperature overnight, cooled to 0° C., and treated with 50 mL of MeOH. After being warmed to room temperature over 1 hour, the solvents are evaporated, and the oil is dried at room temperature under vacuum for 12 hours. It is taken up in 100 mL of THF containing 0.1 g of pTsOH, and the solution is warmed to reflux for 12 hours. The THF is evaporated under reduced pressure, and remaining oil is taken up in 100 mL of $Et_2O$. The $Et_2O$ solution is washed with 2.0N NaOH (3×50 mL) and 50 mL of brine. Drying over $MgSO_4$ followed by evaporation of the solvent gives 4.4 g (80% yield) of 4-cyclopentyl-dihydro-furan-2-one as an oil. NMR ($^1$H, 400 MHz, CDCl$_3$) δ1.1 (2H, m); 1.3–1.8 (7H, m); 2.2 (1H, dd); 1.4 (1H, m); 1.6 (1H, dd); 3.9 (1H, dd); 4.4 (1H, dd).

Step D

Preparation of 3-bromomethyl-3-cyclopentyl-propionic acid ethyl ester—A solution of 4-cyclopentyl-dihydro-furan-2-one (4.4 g, 28.5 mmol) in 100 mL of EtOH is saturated with HBr at 0° C. The mixture is warmed to room temperature overnight. It is diluted with 200 mL of $H_2O$ and extracted with $Et_2O$ (3,100 mL). The combined extracts are washed with brine (2.50 mL) and dried over $MgSO_4$. Evaporation of $Et_2O$ gives 6.4 g (85% yield) of 3-bromomethyl-3-cyclopentyl-propionic acid ethyl ester as a clear oil. NMR ($^1$H, 400 MHz, CDCl$_3$) δ1.1 (2H, m); 1.2 (3H, t); 1.5 (4H, m); 1.8 (3H, m); 1.9 (1H, m); 2.4 (2H, dd); 3.5 (2H, dd); 4.1 (2H,q).

Step E

Preparation of 3-Azidomethyl-3-cyclopentyl-propionic acid ethyl ester—A solution of 3-bromomethyl-3-cyclopentyl-propionic acid ethyl ester (4.4 g, 28.5 mmol) and NaN$_3$ (2.0 g, 31.4 mmol) in 25 mL of DMSO is warmed to 60° C. for 12 hours. The mixture is cooled to room temperature and diluted with 100 mL of $H_2O$. Extraction with $Et_2O$ (3×50 mL) and drying over $MgSO_4$ followed by evaporation of the $Et_2O$ gives 4.8 g (75% yield) of 3-azidomethyl-3-cyclopentyl-propionic acid ethyl ester as an oil. NMR ($^1$H, 300 MHz, CDCl$_3$) δ1.1 (2H, m); 1.2 (3H, t); 1.6 (4H, m); 1.8 (3H, m); 1.9 (1H, m); 2.4 (2H, dd); 3.4 (2H, dd); 4.1 (2H, q).

Step F

Preparation of 4-Cyclopentyl-pyrrolidin-2-one—A solution of 3-azidomethyl-3-cyclopentyl-propionic acid ethyl ester (3.7 g, 16.7 mmol) in 50 mL of MeOH is treated with Raney Nickel under an $H_2$ atmosphere at room temperature. When the theoretical amount of $H_2$ is taken up, the catalyst is removed by filtration and MeOH is evaporated. The remaining solid is recrystallized from hexanes to give 1.5 g (58% yield) of 4-cyclopentyl-pyrrolidin-2-one; mp=117–119° C. NMR ($^1$H, 400 MHz, CDCl$_3$) δ1.1 (2H, m); 1.4–1.6 (4H, m); 1.7 (3H, m); 2.1 (1H, m); 2.3 (1H, m); 2.4 (1H, m); 3.05 (1H, dd); 3.4 (1H, dd). Analysis for C₉H₁₅NO: Calculated: C,70.55; H,9.87; N,9.14. Found: C, 70.80; H,9.47; N,9.09.

Step G

Preparation of 4-Amino-3-cyclopentyl-butyric acid—A solution of 4-cyclopentyl-pyrrolidin-2-one (1.5 g, 9.8 mmol) is warmed to reflux in 100 mL of 6.0N HCl for 18 hours. The HCl is evaporated, and the solid is taken up in 50 mL of H₂O. The insolubles are removed by filtration through Celite® 545 and the filtrate is concentrated to 10 mL. It is passed through a column of Dowex®-50 ion exchange resin (bed volume=30 mL). The column is eluted with H₂O until the eluate is neutral, at which time the column is eluted with 300 mL of 3% NH₄OH. When the eluate becomes basic, 200 mL are collected and evaporated under reduced pressure. The solid remaining is taken up in 50 mL of MeOH (some heating on steam bath required), and the insoluble material is removed by filtration. The filtrate is diluted with 50 mL of EtOAc and allowed to stand at room temperature overnight. The precipitate is collected and dried under vacuum with P₂O₅ to give 1.0 g (59% yield) of 4-amino-3-cyclopentyl-butyric acid; mp=200–201° C. NMR (¹H, 400 MHz, CD₃OD) δ1.2 (2H, m); 1.6 (4H, m); 1.8 (4H, m); 2.3 (1H, dd); 2.5 (1H, d); 2.8 (11H, dd); 3.0 (1H, d). Analysis for C₉H₁₇NO₂: Calculated: C,63.13; H,10.01; N,8.18. Found: C,63.36; H,10.11; N,8.14.

EXAMPLE 4

4(R)-Amino-3-cyclopentyl-butyric Acid

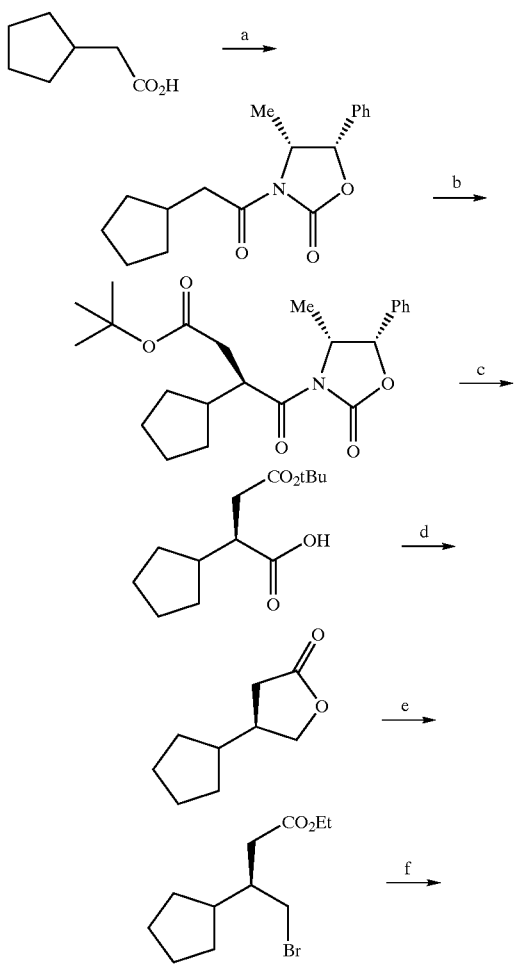

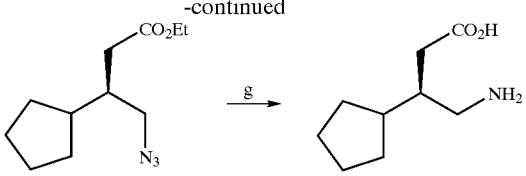

-continued

Step A

Synthesis of (4R,5S)-3-(2-cyclopentyl-ethanoyl)-4-methyl-5-phenyl-oxazolidin-2-one—A solution of cyclopentyl acetic acid (5.0 g, 39 mmol) and triethyl amine (9.86 g, 97.5 mmol) in 150 mL of THF was cooled to −25° C. and treated with pivaloyl chloride (4.7 g, 39 mmol). After 2 hours at −25° C. a solution of (4R,5S)-4-methyl-5-phenyl-oxazolidin-2-one (6.9 g, 39 mmol) in 25 mL of THF and LiCl (1.82 g, 42.9 mmol) was added to the reaction. The reaction was allowed to warm to room temperature and stirred for 18 hours. The reaction was filtered to remove a precipitate, and the filtrate was placed on a rotary evaporator to remove the THF. The residue was partitioned between ethyl acetate and a 1 molar aqueous solution of potassium sulfate. The organic layer was washed with sodium carbonate, water, brine, and dried over magnesium sulfate. The solvent was removed under reduced pressure, and the crude product was purified by column chromatography (4:1 hexane:ethyl acetate) to give the title compound (7.1 g, 80% yield).

Step B (R)-3-Cyclopentyl-4-((4R,5S)-4-methyl-2-oxo-5-phenyl-oxazolidin-3-yl)-4-oxo-butyric acid 4-tert butyl ester—A solution of diisopropyl amine (2.19 g, 21.7 mmol) in 20 mL of THF was cooled to 0° C. and treated with n-butyl lithium (13.5 mL of 1.6 M solution). The solution was cooled to −78° C. and treated with the product from Step A (5.94 g, 20.67 mmol). The reaction was stirred for a 15 minutes and was then placed in a −30° C. bath, treated with tert-butyl bromoacetate (4.23 g, 21.7 mmol), and allowed to stir for 2 hours. The reaction was allowed to warm to room temperature over 12 hours, and the reaction was quenched with aqueous ammonium chloride. The THF was removed under reduced pressure and the residue partitioned between ammonium chloride and ethyl acetate. The organic layer was washed with water, brine, and dried over magnesium sulfate. The solvent was evaporated and the residue chromatographed (2:1 methylene chloride hexane) to give the title compound (8.1 g, 93% yield).

Step C (R)-2-Cyclopentyl-succinic acid 4-tertbutyl ester—A solution of lithium hydroxide (0.47 g, 19.5 mmol) and hydrogen peroxide (8.8 g of 30% solution) in 25 mL of water was cooled to 0° C. and added to a solution of the product from Step B (3.9 g, 9.8 mmol) in 25 mL of THF at 0° C. The reaction was stirred at this temperature for 24 hours and was quenched with 20 mL of a saturated aqueous solution of sodium bisulfite. The THF was removed under reduced pressure, and the resulting aqueous solution was adjusted to pH 11 with 1N sodium hydroxide. The aqueous mixture was extracted with methylene chloride, and the resulting aqueous solution was acidified to pH 4 with potassium biphosphate. The acidified aqueous mixture was extracted with methylene chloride which was dried over sodium sulfate and evaporated to give the title compound (2.0 g, 84% yield).

Step D (R)-4-Cyclopentyl-dihydro-furan-2-one—To a solution of the product from Step C (2.0 g, 8.2 mmol) in 20 mL of THF at 0° C. was added borane dimethylsulfide complex (0.82 mL of a 10 M solution). The reaction was warmed to room temperature and stirred for 24 hours. The reaction was cooled to 0° C. and treated with 50 mL of methanol and the reaction stirred at ambient temperature for 1 hour. The solvents were removed under reduced pressure. The residue was re-dissolved in 50 mL of 50 mL of THF, treated with a catalytic amount of p-toluenesulfonic acid (0.1 g), and heated to reflux for 8 hours. The THF was removed under reduced pressure and the residue dissolved in ether. The organic solution was extracted with 1N sodium hydroxide, brine, and dried over magnesium sulfate. The solvent was evaporated to give the title compound (1.0 g, 79% yield).

Step E (R)-4-Bromo-3-cyclopentyl-butyric acid ethyl ester—A solution of the product from Step D (1.0 g, 6.5 mmol) in 30 mL of ethanol was cooled to 0° C. and saturated with hydrogen bromide gas. The reaction was stirred for 24 hours, cooled to 0° C., and hydrogen gas was again bubbled through the reaction that was then stirred an additional 24 hours at room temperature. The reaction was quenched with 100 mL of water and extracted with ether. The organic layer was dried over magnesium sulfate and the solvent evaporated to give the title compound (1.4 g, 82% yield).

Step F (R)-4-Azido-3-cyclopentyl-butyric acid ethyl ester—A solution of the product from Step E (1.4 g, 5.3 mmol) and sodium azide (0.66 g, 10.1 mmol) in 25 mL of DMSO was heated to 60° C. for 24 hours. The reaction mixture was cooled, diluted with 100 mL of water, and extracted with ether. The organic layer was dried over magnesium sulfate, and the solvents were evaporated. The residue was chromatographed (9:1 hexane:ethyl acetate) to give the title compound (0.9 g, 75% yield).

Step G (R)-4-Amino-3-cyclopentyl-butyric acid—A solution of the product from Step F (0.81 g, 3.6 mmol) in methanol 25 mL is treated with Raney nickel (0.2 g) and placed under 50 psi of hydrogen. After 24 hours the reaction is filtered and the solvent evaporated. The residue is heated to reflux in 50 mL of a 6N HCl solution for 24 hours. The water is removed under reduced pressure, and the residue is resuspended in 20 mL of water and filtered to remove any insoluble material. The filtrate is loaded onto a dowex ion exchange column, and the column is eluted with water until the eluent is neutral. The product is then eluted from the column by washing with 3% ammonium hydroxide. The fractions containing the desired product were evaporated and the residue recrystallized from methanol-ethyl acetate to give the title compound (0.31 g, 50% yield), mp=189–190° C.; NMR ($H^1$, 400 MHz, $CD_3OD$) δ1.2 (2H, m); 1.6 (4H, m); 1.8 (4H, m); 2.3 (1H, dd); 2.5 (1H, d); 2.8 (1H, dd); 3.0 (1H, d).

EXAMPLE 5

(S)-4-Amino-3-cyclopentyl-butyric Acid

This example was prepared in manner starting manner analogous to that of Example 4 starting from (4S,5R)-4-methyl-5-phenyl-oxazolidin-2-one; mp=178–180° C.; NMR ($H^1$, 400 MHz, $CD_3OD$) δ1.2 (2H, m); 1.6 (4H, m); 1.8 (4H, m); 2.3 (1H, dd); 2.5 (1H, d); 2.8 (1H, dd); 3.0 (1H, d).

What is claimed is:

1. A compound selected from 4-Amino-3-cyclopentyl-butyric acid, (R)-4-Amino-3-cyclopentyl-butyric acid or (S)-4-Amino-3-cyclopentyl-butyric acid.

2. A phamaceutical composition comprising a therapeutically effective amount of a compound according to claim 1 and a pharmaceutically acceptable carrier.

3. A method for treating epilepsy comprising administering a therapeutically effective amount of a compound according to claim 1 to a mammal in need of said treatment.

4. A method for treating faintness attacks, hypokinesia, and cranial disorders comprising administering a therapeutically effective amount of a compound according to claim 1 to a mammal in need of said treatment.

5. A method for treating neurodegenerative disorders comprising administering a therapeutically effective amount of a compound according to claim 1 to a mammal in need of said treatment.

6. A method for treating depression comprising administering a therapeutically effective amount of a compound according to claim 1 to a mammal in need of said treatment.

7. A method for treating anxiety comprising administering a therapeutically effective amount of a compound according to claim 1 to a mammal in need of said treatment.

8. A method for treating panic comprising administering a therapeutically effective amount of a compound according to claim 1 to a mammal in need of said treatment.

9. A method for treating pain comprising administering a therapeutically effective amount of a compound according to claim 1 to a mammal in need of said treatment.

10. A method for treating neuropathological disorders comprising administering a therapeutically effective amount of a compound according to claim 1 to a mammal in need of said treatment.

11. A method for treating gastrointestinal damage comprising administering a therapeutically effective amount of a compound according to claim 1 to a mammal in need of said treatment.

12. A method for treating inflammation comprising administering a therapeutically effective amount of a compound according to claim 1 to a mammal in need of said treatment.

* * * * *